United States Patent
Chiabrera et al.

[19]

[11] Patent Number: 5,879,301
[45] Date of Patent: *Mar. 9, 1999

[54] ULTRASONIC BONE ASSESSMENT METHOD AND APPARATUS

[75] Inventors: Alessandro Chiabrera, Genoa, Italy; Jonathan J. Kaufman, Brooklyn, N.Y.

[73] Assignee: Orthologic Corp., Tempe, Ariz.

[*] Notice: The term of this patent shall not extend beyond the expiration date of Pat. No. 5,651,363.

[21] Appl. No.: 897,999

[22] Filed: Jul. 25, 1997

Related U.S. Application Data

[63] Continuation-in-part of Ser. No. 711,336, Sep. 6, 1996, which is a continuation-in-part of Ser. No. 602,410, Feb. 16, 1996, Pat. No. 5,651,363.

[51] Int. Cl.[6] ......................................................... A61B 8/00
[52] U.S. Cl. ............................................ 600/437; 600/449
[58] Field of Search ...................................... 600/437, 449

[56] References Cited

U.S. PATENT DOCUMENTS

| | | | |
|---|---|---|---|
| 3,847,141 | 11/1974 | Hoop ............................................ | 128/2 |
| 4,361,154 | 11/1982 | Pratt, Jr. .................................... | 128/660 |
| 4,774,959 | 10/1988 | Palmer et al. ........................... | 128/660 |
| 4,913,157 | 4/1990 | Pratt, Jr. et al. ......................... | 128/661 |
| 4,926,870 | 5/1990 | Brandenburger ........................ | 128/660 |
| 4,941,474 | 7/1990 | PRatt, Jr. ................................. | 128/660 |
| 4,941,747 | 7/1990 | Dakin ....................................... | 356/346 |
| 4,976,267 | 12/1990 | Jeffcott et al. ........................... | 128/660 |
| 5,054,490 | 10/1991 | Rossman et al. ........................ | 600/449 |
| 5,235,981 | 8/1993 | Hascoet et al. .......................... | 128/660 |
| 5,259,384 | 11/1993 | Kaufman et al. ........................ | 128/660 |
| 5,309,898 | 5/1994 | Kaufman et al. ........................... | 601/2 |
| 5,343,863 | 9/1994 | Wiener et al. ..................... | 128/660.01 |
| 5,458,130 | 10/1995 | Kaufman et al. ........................ | 128/661 |
| 5,651,363 | 7/1997 | Kaufman et al. .................. | 128/660.02 |

*Primary Examiner*—Francis J. Jaworski
*Attorney, Agent, or Firm*—Dykema Gossett PLLC

[57] ABSTRACT

A method for the assessment of various properties of bone is provided. The method includes applying a pair of ultrasound transducers to skin on opposite sides of the bone and generating an ultrasound signal and directing the signal through both the bone and a known medium to obtain a bone output signal and a reference signal. The method further includes establishing a set of parameters associated with the bone output signal and a set of parameters associated with the reference signal and then subjecting the two sets of parameters to comparative analysis in order to obtain the desired bone property. An apparatus for the assessment of various properties of bone is also provided. The apparatus includes a pair of ultrasound transducers which may be single-element transducers or array transducers in any combination. The apparatus further includes various computer hardware components and computer software for generating and directing the ultrasound signal, establishing the parameter sets and performing the comparative analysis.

18 Claims, 4 Drawing Sheets

40
ANATOMICAL LANDMARK
(EDGE OF HEEL BONE)

ns. 5,879,301

ULTRASONIC BONE ASSESSMENT METHOD AND APPARATUS

CROSS-REFERENCES TO RELATED APPLICATIONS

This application is a continuation-in-part of application Ser. No. 08/711,336, filed Sep. 6, 1996, which is a continuation-in-part of application Ser. No. 08/602,410, filed Feb. 16, 1996 and now U.S. Pat. No. 5,651,363.

FIELD OF THE INVENTION

The present invention relates generally to apparatus and method for non-invasively and quantitatively evaluating bone tissue in vivo. More specifically, the invention pertains to osteoporosis diagnosis and bone fracture risk assessment using nonlinear classifiers and multiple ultrasonic features.

BACKGROUND OF THE INVENTION

In recent years, ultrasound has received a great deal of attention as a new technique for noninvasive assessment of bone, and numerous attempts have been made to use ultrasonic energy for evaluating the condition of bone tissue in vivo, and thus for defining a stage of development of osteoporosis and assessing bone fracture risk.

In particular, Hoop discloses in U.S. Pat. No. 3,847,141 a device to measure bone density as a means for monitoring calcium content of the involved bone. A pair of opposed ultrasonic transducers is applied to opposite sides of a patient's finger, such that recurrent pulses transmitted via one transducer are "focused" on the bone, while the receiving response of the other transducer is similarly "focused" to receive pulses that have been transmitted through the bone. The circuitry in Hoop is arranged such that filtered reception of one pulse triggers the next pulse transmission; the filtering is by way of a bandpass filter, passing components of received signals in the 25 kHz to 125 kHz range only; and the observed frequency of retriggering is believed to be proportional to the calcium content of the bone. Thus, Hoop is not concerned with anything more than what he perceives to be transit time for pulses in the indicated band.

Pratt, Jr. deals with establishing, in vivo, the strength of bone in a live being such as a horse. In U.S. Pat. No. 4,361,154, the inventor solves the problem posed by measuring transit time from "launch" to "reception" of pulses of 0.5 MHZ and 1.0 MHZ through the bone and soft tissue, and from measurement of pulse-echo time, to thereby derive a measurement of transit time through bone alone. A data bank enables the evaluation of the meaning of variations in measurements of the transit time which is deduced to be correlated with propagation velocity through each measured bone. U.S. Pat. No. 4,913,157, also granted to Pratt, Jr., operates on the same general principle of transit time/velocity deduction, using the later preferred frequency of 2.25 MHZ as the base frequency of pulsed "launchings" and a technique of matched filtering/Fourier transform filtering for further analyzing received pulses. The bone-transfer function is purported to be derived from analysis of an average of the received pulses. In his U.S. Pat. No. 4,941,474, the inventor further refines his technique of transit time/velocity deduction, inter alia, by separately determining the ratio of the velocity of his observed "bone signal" to the velocity of his observed "soft-tissue signal" making use of the same technique of filtering set forth in his U.S. Pat. No. 4,913,157.

Palmer et al. disclose in U.S. Pat. No. 4,774,959 a bone measurement system deriving the slope of the relation between ultrasonic frequency and attenuation of a sequence of tone signals. Being in the range of 200 to 600 kHz, the signals are applied to one transducer and received by another transducer. The passage of the signals between the two transducers with and without the intervening presence of a heel bone is compared, with the assumption that the frequency/attenuation relation is a straight line, i.e. of constant slope.

U.S. Pat. No. 4,926,870 granted to Brandenburger discloses another in vivo bone-analysis system which depends upon measuring transit time for an ultrasonic signal along a desired path through a bone. A "canonical" wave form, determined by previous experience to be on the correct path, is used for comparison against received signals for transmission through the patient's bone, while the latter is reoriented until the received signal indicates that the bone is aligned with the desired path. Again, ultrasonic velocity through the patient's bone is assumed to have been determined from measured transit time.

Rossman et al disclose in U.S. Pat. No. 5,054,490 an ultrasound densitometer for measuring physical properties and integrity of a bone, upon determination of transit time, in vivo, through a given bone, in comparison with transit time through a medium of known acoustic properties. Alternatively, the Rossman et al. device compares absolute attenuation of specific frequency components of ultrasound acoustic signals through the bone with the absolute attenuation of the same frequency components through a medium of known acoustic properties. For attenuation measurements, a "broad-band ultrasonic pulse" is recommended and is illustrated as a single spike "which resonates with a broadband ultrasonic emission". The necessary comparisons are performed by a microprocessor, resulting in a slope of attenuation versus frequency in the broadband of interest. The frequencies or frequency ranges are not disclosed. Of note, the ultrasound densitometer disclosed in the Rossman, et al, patent is a two-dimensional array transducer consisting of twelve elements. Each element is activated individually by an ultrasound acoustic signal.

The prior art, exemplified by the above references that have been briefly discussed, proceed on the assumptions that transit time is all-important in assessing acoustic velocity or that only one or a few specific ultrasonic frequencies are significant in the determination of the attenuation versus frequency "slope" of a presumably linear relationship. These approaches have been essentially ad hoc, with no consistent framework within which to analyze data. Despite the fact that a rich variety of information is obtainable from experiments with ultrasound, much of the information has not been used and available, and useful aspects of the data have been ignored.

A step forward in this direction was made by Kaufman et al., who disclosed in U.S. Pat No. 5,259,384 an apparatus and method for quantitatively evaluating bone tissue in vivo. Whereas the prior methods have relied on rather simplistic analyses techniques, the method of Kaufman et al. disclosed in the U.S. Pat. No. 5,259,384 Patent includes iterative subjecting bone to an ultrasonic acoustic excitation signal pulse of finite duration, supplied to one of two transducers on opposite sides of the bone, and involving a signal consisting of plural frequencies in the ultrasonic region to approximately 2 MHZ; the excitation signal is repeated substantially in the range from 1 to 1000 Hz. Signal processing of received signal output of the other transducer is operative (a) to sequentially average the most recently received given number of successive signals to obtain an averaged per-pulse signal and (b) to produce a Fourier transform of the averaged per-pulse signal. In a separate operation not involving the bone, the same transducers respond to the transmission and reception of the same excitation signal via a medium of known acoustic properties and path length to establish a reference signal, and this reference signal is processed to produce a Fourier transform of the reference signal.

The two Fourier transforms in the U.S. Pat. No. 5,259,384 Patent are comparatively evaluated to produce a bone-transfer function, and the bone-transfer function is processed to derive the frequency-dependent specific-attenuation function $\mu(f)$ and the frequency-dependent group-velocity function $v_g(f)$ associated with the bone-transfer function. Specifically, the frequency-dependent group-velocity function $v_g(f)$ is related to the derivative of the phase of the bone-transfer function, as a function of frequency. Finally, a neural network, configured to generate an estimate of one or more of the desired bone-related quantities, is connected for response to the specific-attenuation function $\mu(f)$ and to the group-velocity function $v_g(f)$, to thereby generate the indicated estimates of the status of the bone that is being analyzed.

All advantages of the last-mentioned apparatus and method notwithstanding, they do not use statistically optimal techniques and therefore may be subject to substantial inaccuracies. In addition, their implementation with the use of current ultrasound devices is still relatively complex and costly, although simpler than that using X-ray densitometric systems.

In addition to the failure of prior art to use all of the available information from ultrasonic assessment, the prior art has predominantly relied on the use of single element transducers. One notable exception was Rossman, et. al, U.S. Pat. No. 5,054,490 as mentioned supra, although Rossman et. al still use standard ultrasonic transit time and attenuation slope ("BUA") techniques. The use of single element transducers makes it difficult to obtain reproducible ultrasound parameter estimates. As a result, it is more difficult to make accurate and precise estimates of bone density, bone strength, bone architecture, bone quality and fracture risk and to make intrapatient and interpatient comparisons based on such estimates.

SUMMARY OF THE INVENTION

It is accordingly a primary object of this invention to provide an improved method and apparatus for characterizing and determining non-invasively the properties of bone. A more particular though not limiting object of the invention is to provide a method and apparatus for non-invasive and quantitative evaluation of bone tissue in vivo, to make accurate osteoporosis diagnosis possible.

A principal object of the present invention resides also in providing a method for bone tissue evaluation and the osteoporosis diagnosis which may be performed in a statistically optimal fashion, and an apparatus for practicing the method.

Another object is to meet the above object in such a way that the bone tissue evaluation and the osteoporosis diagnosis may be performed with relatively more simple and inexpensive means than those previously used.

It is also a general object of the invention to achieve the foregoing objects with apparatus components that are for the most part commercially available.

As compared with the prior art, the invention takes a more rigorous and comprehensive approach. In particular, the present invention is based on both statistical techniques as well as multidimensional parametric methods. On the contrary, the prior art has used basically a (suboptimal) estimate of the linear slope of the ultrasound attenuation, termed broadband ultrasound attenuation (BUA) in most prior art work. This BUA parameter neither appropriately nor completely characterizes all of the information contained in the ultrasound measurements, and therefore cannot meet the objectives of the present invention.

Accordingly, the present invention utilizes a parametric framework to capture as much of the information contained in the ultrasound measurements as possible, to more accurately and precisely determine the characteristics of the interrogated bone (to thereby determine one of the bone properties such as fracture risk, strength, density, quality, and/or architecture of the bone). The advantage of such a signal processing technique is its inherent insensitivity to the presence of multiple reflections, as between the soft tissue and bone interfaces. This is in contrast to the prior art which uses Fourier transform techniques and which is significantly affected by the choice of time frame. The present invention is based on analysis of the primary ultrasound waveform, and thus is not significantly affected by multiple reflections, other modes of propagation, or other artifacts in the received ultrasound signal. The present invention also discloses the use of simplified ultrasound parameter sets which do not require the signals to be digitally sampled and/or stored. This is a crucial advance over the prior art, especially with respect to the implementation of array techniques, where large amounts of data need to be processed. Another advantage of the present invention is that it does not make any a priori assumptions as to the functional dependence of the attenuation, e.g., linearity in the case of the "overused" BUA parameter. Thus, nonlinear attenuation characteristics can be measured with the techniques disclosed below in the present invention.

Furthermore, the prior techniques have relied on "pulse transit time" as a measure of the bone properties. In contrast, the present invention relies on the fact that the parametric signal modeling techniques disclosed below are phase sensitive in nature and thereby take into account the overall phase spectrum associated with the bony member. Thus, whereas the pulse transit time conveys little phase specific information, the disclosed methods are phase comprehensive in nature by design. In addition, the differential phase spectrum and the pulse delay parameter are also used as means for non-invasively determining the properties of the interrogated bone. This allows for enhanced discrimination of the bone properties compared to that obtained using "pulse transit time" alone.

Additionally, to achieve enhanced diagnostic capabilities, the results obtained through the use of the parametric methods disclosed in the present invention can be subsequently processed in different ways including multivariate (linear and nonlinear) regressions, neural networks, and statistical pattern recognition techniques. And finally, the methods disclosed here can be implemented through the use of both digital and analog techniques.

Finally, as compared with the prior art, the invention provides the means by which to obtain more reproducible ultrasound parameter estimates. This is accomplished through the use of multi-element, two-dimensional array transducers in one embodiment of the invention. The prior art has predominantly relied on single element transducers. It is difficult, however, to physically position a transducer in the same relative location on the same patient or patients in subsequent examinations. Multi-element, two-dimensional array transducers enable a clinician to "electronically" position the transducers in approximately the same position each time by locating an anatomical landmark, for example, the edge of a heel bone. In this manner, improved reproducibility and precision in ultrasound parameter estimates can be accomplished. This improvement can lead to more precise and accurate estimates of bone density, bone strength, bone architecture, bone quality and fracture risk, and also improve intrapatient and interpatient comparisons. The ability to carry out intrapatient comparability is particularly important when monitoring a patient over the course of treatment, for example with osteoporosis. Similarly, interpatient comparisons are important when screening a large group of individuals for disease, such as with osteoporosis. Furthermore, the multi-element, two-dimensional array transducers can be utilized in a synthetic array aperture mode in which a single ultrasound acoustic signal is passed through a plurality of elements, also known as the aperture. By moving the aperture one element at a time across the array, high resolution images are made possible, but a high signal to noise ratio and beam collimation can also still be maintained.

In an alternative, single-array transducer embodiment of the invention, only one of the transducers, preferably the receiving transducer, is an array transducer while the other is a single-element transducer. A single-array transducer embodiment is less complex, much easier to implement and much less expensive than the dual-array transducer embodiment, yet retains most of the advantages of the dual-array embodiment, in terms of enhanced reproducibility and accuracy, as compared to embodiments utilizing a pair of single-element transducers. The single-array transducer embodiment can be used with a variety of signal processing methods including standard transit-time, velocity, and attenuation slope techniques, such as BUA, as well as the parametric modeling technique disclosed herein. The single-array transducer embodiment will lead to significant improvements in accuracy and precision when used with any of these signal processing methods.

In summary, the present invention disclosed herein improves significantly on the prior art and will be useful in determining the following tissue characteristics: bone density, bone strength, bone architecture, bone quality and fracture risk as well as other characteristics of bone tissue and other tissues.

The invention in its presently preferred form of a method of non-invasive and quantitative assessment of the status of a bone tissue in vivo for one or more of the quantities: bone-mineral density, strength, and fracture risk, achieves the foregoing objectives by acoustically coupling a pair of transducers to nearby skin surfaces on opposite sides of a bone tissue; generating an ultrasound excitation signal and directing this signal from one transducer to another transducer of the pair of transducers through the bone tissue, and independently through a medium with known acoustic properties and path length and free of the bone tissue, thereby producing a bone-oriented electrical output signal and a reference output signal, respectively, of the form of $z_s(t) = p_s(t) + n_s(t)$ and $Z_r(t) = p_r(t) + n_r(t)$, correspondingly, where $p_s(t)$ and $p_r(t)$ are, respectively, the bone-oriented output signal per se and the reference output signal per se, and $n_s(t)$ and $n_r(t)$ are additive, uncorrelated Gaussian measurement noises associated with these bone-oriented and reference signals, respectively, the excitation signal being a finite-duration signal repeated substantially in a range from 1 to 1000 Hz and consisting of plural frequencies spaced in an ultrasonic spectral region up to about 2 MHz; parametric modeling the bone-oriented and reference signals, with obtaining two parametric models of these signals, $p_s(t)$ and $p_r(t)$, respectively, to thereby establish a set $\Theta_s$ of bone-oriented parameters and a set $\Theta_r$ of reference parameters correspondingly associated with these models; and subjecting the two sets of parameters to comparative analysis resulting in obtaining of an estimate of the one or more quantities.

The parametric model of the bone-oriented output signal may have the form of $$p_s(t) = (A_{s0} + A_{s1}(t-\tau_s) + \ldots + A_{si}(t-\tau_s)^i) exp[-a_s(t-\tau_s)] \sin[2\pi f_s(t-\tau_s)]$$

for $t \geq \tau_s$, and zero otherwise, the set $\Theta_s$ of bone-oriented parameters being $\{A_{s0}, A_{s1}, \ldots A_{si}, a_s, f_s, \tau_s\}$, or $$p_s(t) = (K_{s0} + K_{s1}(t-\tau_s) + \ldots + K_{sm}(t-\tau_s)^m) exp[-b_s(t-\tau_s)^2] \sin[2\pi f_s(t-\tau_s)]$$

the set $\Theta_s$ being $\{K_{s0}, K_{s1}, \ldots, K_{sm}, b_s, f_s, \tau_s\}$.

For the preferred embodiment, the form of the bone-oriented signal model may respectively be $$p_s(t) = (A_{s0} + A_{s1}(t-\tau_s) + A_{s2}(t-\tau_s)^2) exp[-a_s(t-\tau_s)] \sin[2\pi f_s(t-\tau_s)]$$

for $t \geq \tau_s$, and zero otherwise, the set $\Theta_s$ being $\{A_{s0}, A_{s1}, A_{s2}, a_s, f_s, \tau_s\}$, or $$p_s(t) = (K_{s0} + K_{s1}(t-\tau_s) + K_{s2}(t-\tau_s)^2) exp[-b_s(t-\tau_s)^2] \sin[2\pi f_s(t-\tau_s)]$$

the set $\Theta_s$ being $\{K_{s0}, K_{s1}, K_{s2}, b_s, f_s, \tau_s\}$.

The parametric model of the reference signal may have the form of $$p_r(t) = (A_{r0} + A_{r1}(t-\tau_r) + \ldots + A_{rj}(t-\tau_r)^j) exp[-a_r(t-\tau_r)] \sin[2\pi f_r(t-\tau_r)]$$

for $t \geq \tau_r$, and zero otherwise, the set $\Theta_r$ of reference parameters being $\{A_{r0}, A_{r1}, \ldots A_{rj}, a_r, f_r, \tau_r\}$, or the form of $$p_r(t) = (K_{r0} + K_{r1}(t-\tau_r) + \ldots + K_{rq}(t-\tau_r)^q) exp[-b_r(t-\tau_r)^2] \sin[2\pi f_r(t-\tau_r)]$$

the set $\Theta_r$ being $\{K_{r0}, K_{r1}, \ldots K_{rq}, b_r, f_r, \tau_r\}$.

For the preferred embodiment, the form of the reference signal model may respectively be $$p_r(t) = (A_{r0} + A_{r1}(t-\tau_r) + A_{r2}(t-\tau_r)^2) exp[-a_r(t-\tau_r)] \sin[2\pi f_r(t-\tau_r)]$$

for $t \geq \pi_r$, and zero otherwise, the set $\Theta_r$ being $\{A_{r0}, A_{r1}, A_{r2}, a_r, f_r, \tau_r\}$, or $$p_r(t) = (K_{r0} + K_{r1}(t-\tau_r) + K_{r2}(t-\tau_r)^2) exp[-b_r(t-\tau_r)^2] \sin[2\pi f_r(t-\tau_r)]$$

the set $\Theta_r$ being $\{K_{r0}, K_{r1}, K_{r2}, b_r, f_r, \tau_r\}$.

The set $\Theta_r$, of bone-oriented parameters and the set $\Theta_r$ of reference parameters are estimated with the use of a least square optimization algorithm, to thereby provide a maximum likelihood estimates $\Theta_{s,ML}$ and $\Theta_{r,ML}$ defined as $$\Theta_{s,ML} = \operatorname{argmin} J_s(\Theta_s) = \operatorname{argmin}\left[\sum_{i=0}^{N} [z_s(t_i) - p_s(t_i)]^2\right]$$

and $$\Theta_{r,ML} = \operatorname{argmin} J_r(\Theta_r) = \operatorname{argmin}\left[\sum_{i=0}^{N} [z_r(t_i) - p_r(t_i)]^2\right]$$

respectively, where argmin denotes a value of the bone-oriented and reference parameters which provide smallest values of the sums $\Sigma$.

The step of comparative analysis may be performed with the use of one or more of a plurality of associated parameters: age, bony member thickness, sex, height, weight specific for an individual patient.

Also, a preprocessing step prior to the step of comparative analysis may be added, inputs of the preprocessing step being the two sets of parameters of the models and an output of the preprocessing step being a reduced set of parameters characterizing these models.

The one or more of the plurality of associated parameters specific for an individual patient may be also input to the preprocessing step.

The preprocessing step may include determination of an optimal transfer function estimate, this estimate being the output of the preprocessing step.

The comparative analysis may be performed with the use of a neural network configured to generate an estimate of the one or more of the quantities from the sets of parameters and from the associated parameters specific for an individual patient.

Also, the comparative analysis may be performed with the use of multivariate regressions or a statistical hypothesis testing algorithm.

In its presently preferred apparatus form, the invention comprises transducer means including a pair of ultrasonic transducers adapted for acoustic coupling to nearby skin and for transmission through an ascertained acoustic propagation path which includes a bony part of a living body; a generator means for connecting to a transmission transducer of the pair to apply an excitation signal to the bony part, this signal being a finite-duration signal consisting of plural frequencies spaced in the ultrasonic spectral region to approximately 2 MHZ and being repeated substantially in the range from 1 Hz to 1000 Hz; and a signal-processing means that are connected for response to the signal received by a receiving transducer of the pair and comprise means to provide parametric modeling of the bone-oriented and reference signals, to thereby produce corresponding sets of parameters associated with the models of the bone-oriented and reference signals, means to provide preprocessing of the sets resulting in a reduced set of parameters associated with the above two types of signals, means for performing comparative analysis of the parameters resulting in estimates of bone properties, as well as means for determining transfer function, group delay, group velocity and polynomial coefficients used for comparative analyses, and means for zero-crossing, Fourier transform and Hilbert transform analyses.

With these and other objects and advantages in view, the present invention will be clearly understood from the ensuing detailed description in connection with the drawings.

DETAILED DESCRIPTION OF THE PREFERRED EMBODIMENT

Figure 1:
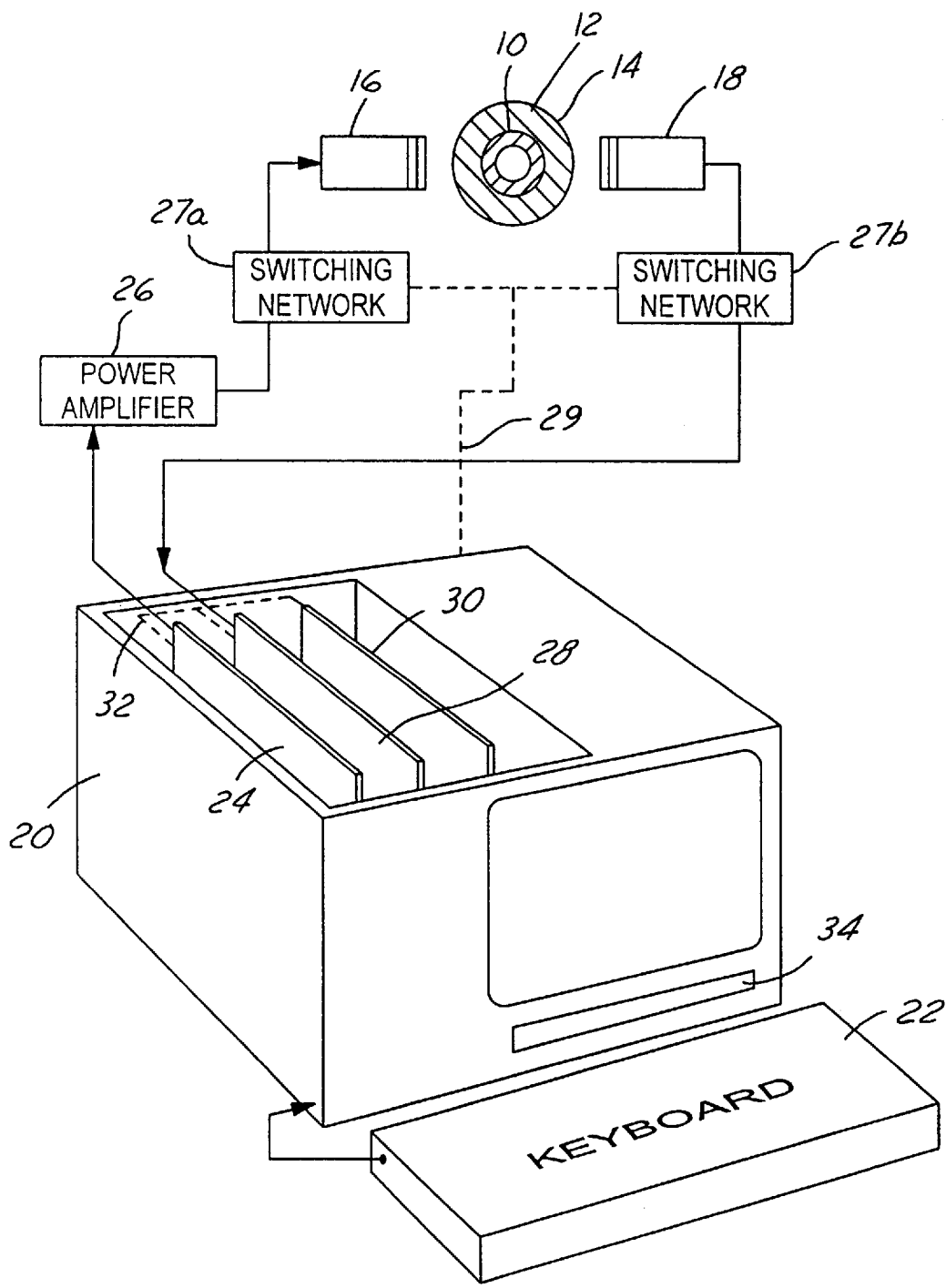
FIG. 1 is a block diagram showing the interconnections of components of an apparatus of the invention.

The invention is shown in FIG. 1 as applied to interconnected components for constructing an apparatus for practicing a method of the invention. Specifically, it is intended for non-invasively and quantitatively evaluating the status of bone tissue in vivo, as manifested through one or more of the quantities: bone-mineral density, strength, and fracture risk at a given time. The components of the apparatus are, in general, commercially available from different sources and will be identified before or in the course of the detailed description of their total operation.

Referring to FIG. 1, a bone locale 10 to be analyzed in vivo is shown surrounded by a soft tissue 12 having an outer skin surface (skin integument) 14. The bone locale (part) 10 is to be interposed between two aligned and opposed ultrasonic transducers 16 and 18, which may be identically the same, and can be obtained from Panametrics, Inc., Waltham, Mass.; suitably, each of the transducers 16, 18 may be Panametrics VIDEOSCAN part number V318-SU, having a nominal element size of ¾-inch diameter, and rated for 500 kHz. As shown, the transducer 16 is used for signal launching and the transducer 18 is the receiver for the launched signals after passing through the bone part 10, its surrounding soft tissue 12, and a coupling medium such as a gel (not shown) between each transducer face and the outer skin surface 14 of the soft tissue 12.

Basic operation is governed by a computer means 20, which may be a personal computer, such as the 25 MHZ '386 PC available from Gateway 2000, Inc. North Sioux City, S.Dak.; as its designation suggests, this computer contains a 25 MHZ clock-pulse generator, and an Intel 80386 processor, with provision for keyboard instruction at 22.

An arbitrary-function generator card 24 is shown installed in the computer 20. This card is relied upon to generate an excitation signal which is periodically supplied to the launch transducer 16, via a power amplifier means 26. The power amplifier 26 is suitably the Model No. 240L, an RF power-amplifier product of EIN, Inc., Rochester, N.Y. This amplifier provides a 50 dB gain, over the range 20 kHz to 10 MHZ. In addition to power amplifier means 26, the excitation signal must pass through a switching network 27a in an alternative embodiment using multi-element, two-dimensional array transducers, described fully infra.

The excitation signal generated by the card 24 is a finite-duration signal, consisting of plural frequencies that are spaced in the ultrasonic spectral region to approximately 2 MHZ. The signal is repeated substantially in the range from 1 to 1000 Hz. The card 24 may suitably be a waveform synthesizer, a product of Quatech, Inc., Acron, Ohio, identified by Quatech part No. WSB-100. The waveform synthesizer provides generation of analog signals independent of the host computer 20, that allows full processor power to be used for other tasks, including calculation of waveform data. It has the capacity to generate an output signal comprising literally thousands of points in the indicated ultrasonic frequency region.

Another card 28 is shown installed into the computer 20 for converting signals received at the receiving transducer 18 into a digital format for further processing in the computer 20. The card 28 may suitably be a 100 MHZ waveform digitizer, a part No. "STR*8100", a product available from SONIX, of Springfield, Va. As with the launch transducer 16, in an alternative embodiment described more fully infra, where receiving transducer 18 is a multi-element, two-dimensional array transducer, a switching network 27b must be placed between the receiving transducer 18 and the card 28 of computer 20.

One more card 30 (such as National Instruments of Austin, Tex., Model No. AT-MIO-16-E-1) is to be installed into the computer 20 to count zero crossings in the received signal for further processing the feature parameter in the computer 20. Alternatively, a stand-alone device such as frequency counter PM 6681 available from Fluke Mfg. Co., Inc., Everett, Wash., can be used for performing this function. A connection 32 shown by dashed lines is used for synchronizing the generator card and for the purposes of digitizing the excitation signals, to enable computer 20 to perform a suitably compensated, continuously operative updating average of the signals received at the receiving transducer 18.

Also, general signal-processing/display/storage software, for the signal processing control and operation of the computer 20 is not shown but will be understood to be a floppy disk loaded at 34 into the computer 20; this software is suitably MATLAB for Windows, available from The Math Works, Inc., Natick, Mass. Further software, also not shown but loaded into the computer 20, is neural-network software, identified as EXPLORENET 3000, a product of HNC, Inc., San Diego, Calif., and the Optimization Toolbox (also from Math Works).

In the presently preferred embodiment, involving the described components of FIG. 1, the same components are utilized not only for performing the continuously updated averaging of the latest succession of signals received at the receiving transducer 18 after they have passed through a bone member 10-12-14, but also for establishing and entering into computer storage the data of a reference signal that is obtained by removing the body member 10-12-14 from the space between the transducers 16, 18 and replacing it with a medium with known acoustic properties, such as water, and known path length.

The specific signal used for transmitting through the bone member 10-12-14 is selected such that after propagating through the bony member the received ultrasound waveform, $p_s(t)$, has the form that can be represented by the following parametric signal model:

$$p_s(t)=(A_{s0}+A_{s1}(t-\tau_s)+\ldots+A_{si}(t-\tau_s)^i)exp[-a_s(t-\tau_s)]\sin[2\pi f_s(t-\tau_s)] \quad (1)$$

for $t \geq \tau_s$ and zero otherwise. A similar model is used for the reference signal, $p_r(t)$, namely, $$p_r(t)=(A_{r0}+A_{r1}(t-\tau_r)+\ldots+A_{rj}(t-\tau_r)^j)exp[-a_r(t-\tau_r)]\sin[2\pi f_r(t-\tau_r)] \quad (2)$$

for $t \geq \tau_r$, and zero otherwise. It will be appreciated that all of the information contained in this ultrasound diagnostic experiment is contained in the two sets of parameters associated with the above two signal models, namely, $\{A_{s0}, A_{s1}, \ldots A_{si}, a_s, f_s, \tau_s\}$ and $\{A_{r0}, A_{r1}, \ldots A_{rj}, a_r, f_r, \tau_r\}$, at least insofar as the two signal models provide accurate representations of the measured data. In general, the parameters associated with the bony member and reference ultrasound signals will be denoted by $\Theta_s$ and $\Theta_r$, respectively. It has been found by the inventors of the present invention that in many cases these particular mathematical descriptions, i.e. Equations (1–2) are good models for the ultrasound measurements. In these cases, the parameters and $\Theta_s$ and $\Theta_r$ provide an effective means for characterizing the information obtained in the ultrasound diagnostic experiment, without being bound by the assumptions of the linear (BUA) model. It is to be understood that the linear BUA feature used almost universally in the prior art of ultrasound bone assessment represents a significant loss of information. This information has been found to be critically important for and relevant to bone assessment. Moreover, the parameters in the presently described invention may be estimated using one of various statistical procedures, most preferably with the method of maximum likelihood, which can provide minimum variance estimates, together with a measure of the quality of the estimates. This method of estimation is by itself well known, and *Detection, Estimation, and Modulation Theory, Part I Detection, Estimation, and Linear Modulation Theory*, by H. L. van Trees, McGraw Hill, New York, 1968, may serve a good reference for both the maximum likelihood estimation and statistical decision theory. The approach of the present invention is also in evident comparison to the relatively ad hoc methods used previously which are not based on any optimal estimation procedure at all. Indeed, the evaluation of BUA, which already discards a significant amount of information, is based on an arbitrarily chosen frequency range and without taking into account the statistics of the modeling errors. In contrast, the present invention imposes no specific frequency range. Rather, the frequency range over which the signal parameters are determined arises out of the parametric methods disclosed herein. The present invention represents a significant step forward in these regards as well.

The present inventors have found it useful also to employ different signal models in order to most accurately represent different ultrasound signals, these models containing different signal parameters. For example, another parametric signal model which has proved effective for characterizing the ultrasound data is $$p_s(t)=(K_{s0}+K_{s1}(t-\tau_s)+\ldots+k_{sm\ exp[-bs](t-\tau_s\})^2]\sin[2\pi f_s(t-\tau_s)] \quad (3)$$

with an analogous equation for the reference signal, $p_r(t)$, i.e., $$p_r(t)=(K_{r0}+K_{r1}(t-\tau_r)+\ldots+K_{rq}(t-\tau_r)^q)exp[-b_r(t-\tau_r)^2]\sin[2\pi f_r(t-\tau_r)] \quad (4)$$

Figure 2:
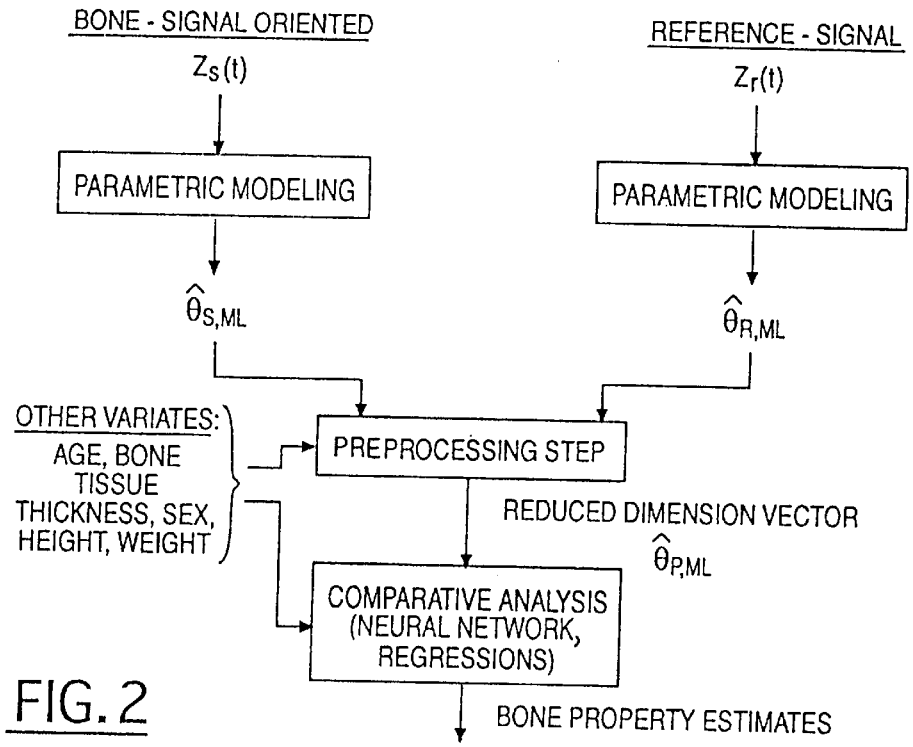
FIGS. 2–4 are flow charts of computer-controlled operations in automatically analyzing and quantitatively reporting estimates of relevant bone-related factors.
Figure 3:
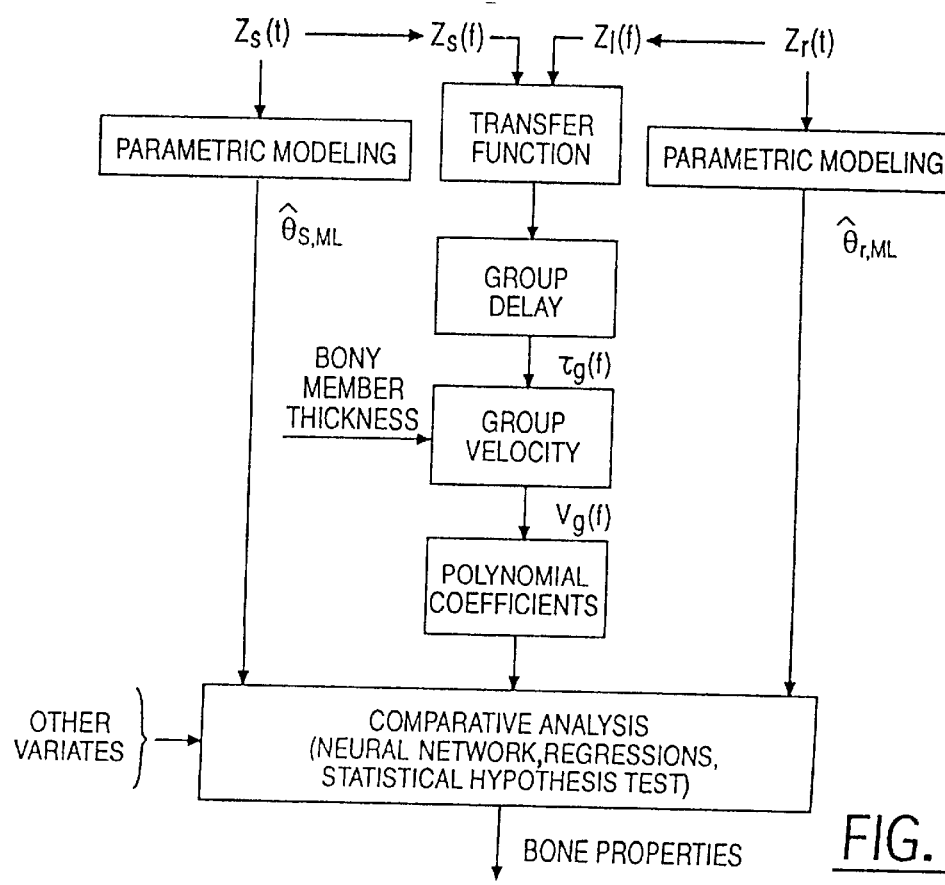
Figure 4:
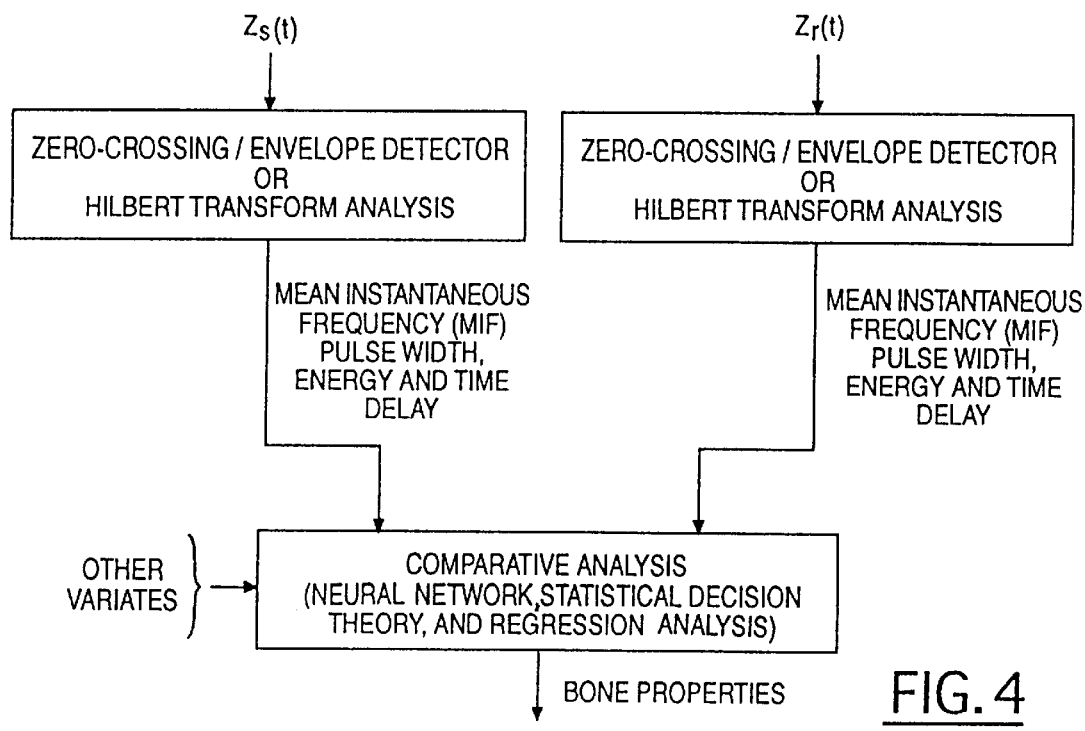

In this instance, the two sets of model parameters are given by $\{K_{s0}, K_{s1}, \ldots K_{sm}, b_s, f_s, \tau_s\}$ and $\{K_{r0}, K_{r1}, \ldots K_{rq}, b_r, f_r, \tau_r\}$. The signal models as given above in Equations (1–4) are shown using polynomials of an order which is selected depending on the specific ultrasound signal being modeled. It is advisable, for the purposes of the preferred embodiment described in the present specification, to select this order (the value of i, j, m, and q) to equal two (2). Additionally, it is not necessary to use the same signal model for the reference and bone member ultrasound signals, respectively. For example, the reference signal may be characterized by Equation (4) while the ultrasound signal which has propagated through the bony member may be characterized by Equation (1). These two respective sets of parameters are, in the presently preferred embodiment of the invention, further processed to obtain estimates of the bone properties of interest. It should be pointed out that the two sets of signal parameters, $\Theta_s$ and $\Theta_r$, may initially be preprocessed, as shown in FIGS. 2–4 which illustrate the method invention, to obtain a smaller set of parameters (reduced dimension vector), which smaller set may then serve as input to a final processing step. In such an alternative embodiment of the invention, this preprocessing step may result in an optimal (e.g., maximum likelihood) transfer function estimate, and it is this transfer function estimate which serves as input to the final comparative analysis step. In general, this transfer function estimate may be characterized by a fewer number of parameters than the original two ultrasound signal parameter sets. It is appreciated that the transfer function estimate retains the maximum likelihood property, due to the property of invariance of maximum likelihood estimates.

With the signal parameter sets, i.e., $\Theta_s$ and $\Theta_r$, being able to be obtained in a number of ways, either in the frequency or in the time domain, in the currently preferred embodiment, a time domain approach is used since it gives the maximum likelihood estimates in the most direct fashion. In particular, it is assumed that the ultrasound measurements, i.e., $z_s(t)$ and $z_r(t)$, can be represented by the following two equations:

$$z_s(t)=p_s(t)+n_s(t) \quad (5)$$

and $$z_r(t)=p_r(t)+n_r(t) \quad (6)$$

where $p_s(t)$ and $p_r(t)$ are the bone-oriented ultrasound signal per se and the reference ultrasound signal per se, respectively, whereas $n_s(t)$ and $n_r(t)$ are additive, uncorrelated Gaussian and mutually independent measurement noises associated with the bone-oriented and reference ultrasound signals, respectively. Then, in the presently preferred embodiment, the signal parameters are estimated using the principle of least squares, which under the above assumptions provides the maximum likelihood estimates, $\Theta_{s,ML}$ and $\Theta_{r,ML}$, viz., $$\Theta_{s,ML} = \mathrm{argmin} J_s(\Theta_s) = \mathrm{argmin}\left[\sum_{i=0}^{N}[z_s(t_i)-p_s(t_i)]^2\right] \quad (7)$$

and $$\Theta_{r,ML} = \mathrm{argmin} J_r(\Theta_r) = \mathrm{argmin}\left[\sum_{i=0}^{N}[z_r(t_i)-p_r(t_i)]^2\right] \quad (8)$$

The optimal parameter values may be attained using any of a variety of nonlinear least square optimization algorithms, for example using the Optimization Toolbox from the MATLAB software available from The Math Works, Inc., Natick, Mass.

In Equations (7–8), argmin denotes the value of the parameters which provides the smallest value of the sums $\Sigma$ enclosed in square brackets. Comparative analysis of the above two sets of signal parameters is used to non-invasively diagnose the physical state of bone being examined, as well as to compare one patient with another, in terms of their relative fracture risk, bone density, bone strength or bone architecture. This analysis can be as simple as comparing values obtained in a database of numerous patients with and without disease, e.g., with and without osteoporosis, or more complex analyses using multivariate linear or nonlinear regressions, and most generally, a neural network. It can also include an optimal statistical hypothesis test, in terms of detecting whether or not a patient has osteoporosis, based on the respective ultrasound signal parameter set.

For example, in a currently preferred embodiment, a neural network serves to estimate both the bone fracture risk and bone mineral density of a particular patient. Neural network is an information processing device that utilizes a large number of simple modules, and in which information is stored by components that at the same time effect connections between these modules. Neural networks are well known in the art (the reference can be made to *Neural Networks, A Comprehensive Foundation*, by Simon Haykin, IEEE Press, Macmillan College Publishing Company, New York, 1994). They are appreciated for their remarkable ability to derive meaning from complicated or imprecise data and are usually used to trace trends that are too complex to be noticed by either humans or other computer techniques.

The inputs to the neural network are the four (4) maximum likelihood parameter estimates of the reference ultrasound signal modeled by Equation (4) and the six (6) maximum likelihood parameter estimates of the bone ultrasound signal modeled by Equation (1), for a total of 10 neural network inputs. It is pertinent to note once again that the maximum likelihood property is retained once it has been acquired, due to the property of invariance of maximum likelihood estimates. The outputs of the neural network are bone fracture risk and bone mineral density, in this currently preferred embodiment. The neural network was trained using data provided from 100 patients, in order to determine an appropriate set of neural network parameters.

In yet another alternative, additional information can be used as inputs to the neural network, to the multivariate regressions, or to the statistical hypothesis testing algorithm. These additional inputs may include the thickness of the bony member, weight, height, age, and other variates associated with each individual patient.

In an alternative embodiment of the invention, a simpler estimation procedure can be used to obtain estimates of the signal parameters or some subset of the signal parameters. In this embodiment, the frequencies, $f_s$ and $f_r$, are estimated using the mean instantaneous frequency (MIF) obtained with the Hilbert transform. Specifically, the received ultrasound signals, $z_s(t)$ and $z_r(t)$, are first processed to obtain their associated Hilbert transforms, namely $z_{sH}(t)$ and $z_{rH}(t)$. The complex analytic signals $z_{sA}(t)$ and $z_{rA}(t)$ associated with $z_s(t)$ and $z_r(t)$, respectively, are then obtained as:

$$z_{sA}(t)=z_s(t)+jz_{sH}(t) \quad (9)$$

and $$z_{rA}(t)=z_r(t)+jz_{rH}(t) \quad (10)$$

where $j=(-1)^{1/2}$. From Equations (9–10), the mean instantaneous frequencies associated with the received ultrasound signals may be evaluated from their real and imaginary parts and used as approximate estimates of the signal parameters, $f_s$ and $f_r$. In addition, the envelopes of the received signals may be evaluated as the magnitude of the analytic signals of Equations (9–10) and provide simplified estimates of the exponential signal parameters. In particular, the time durations of the respective envelopes provide approximate inverse values for the respective parameters $a_s$ and $a_r$, or $b_s$ and $b_r$. Though this alternative embodiment is somewhat more susceptible to noise than the maximum likelihood approach disclosed above, it may, on the other hand, be implemented in analog and in "real time."

An even simpler alternative embodiment does not incorporate the Hilbert transform but rather relies on simplified zero-crossing analysis and envelope detection methods, for example, diode rectification followed by low-pass filtering. In this case, estimates of the same set of parameters can be made, e.g., $f_s$ and $f_r$, $a_s$ and $a_r$, or $b_s$ and $b_r$. Using the zero crossing analysis, an average frequency content in a received ultrasonic signal, approximately equal to the MIF, is defined within a measurement interval. In addition, the time duration of the envelope is also a feature related to the characterization of the bone tissue. This feature is related to the exponents a and b in the two different signal parameterizations. The quantitative ultrasonic feature parameter $\beta$ combining a MIF for the signal that propagated through the bone tissue and a $\mathrm{MIF}_{REF}$ for the ultrasonic reference signal is then calculated, i.e. $\beta=1-\mathrm{MIF}/\mathrm{MIF}_{REF}$. This parameter typically increases with increasing BUA, although it depends in a more complex fashion on the nonlinear dependence of ultrasonic attenuation on frequency. It is, however, also indicative of the amount of bone present in the acoustic propagation path. This alternative embodiment leads to an even more simplified real-time hardware implementation but with a trade off as to statistical precision and accuracy. In general, the above ultrasonic features are related to the mean frequency content and spectral bandwidth of the bone-oriented signal and reference signal, respectively. Another useful feature, in addition to the above, is the overall energy content of the received ultrasonic bone-oriented and reference signals. Finally, the time delays of the respective ultrasonic pulses can provide some additional information useful for characterizing the bone tissue. It should be also understood that any subset of the ultrasonic features may serve as input to the subsequent comparative processing technique, as with neural networks or multivariate regression.

As has been pointed out, the above methods may also be implemented completely or partly in the frequency (spectral) domain, but the results are essentially the same. Which method is to be preferred depends on the type of hardware and software available.

An additional aspect of the present invention relates to the use of the group delay associated with the ultrasound data. As already noted, the two sets of ultrasound signal parameters include time delay parameters, $\tau_s$ and $\tau_r$. These parameters are related to the differential phase associated with the phase difference of the reference and bone signals, respectively. In an alternative embodiment of the invention, a direct estimate of the differential phase may be substituted for the time delay parameters in the final comparative analysis. This differential phase is evaluated from the ratio of the Fourier transforms of the reference and bone signals, respectively. Specifically, if $Z_s(f)$ and $Z_r(f)$ are the Fourier transforms of the bone and reference ultrasound signals, respectively, then $$H(f) = \frac{Z_s(f)}{Z_r(f)} \quad (11)$$

where $H(f)$ is the complex frequency dependent transfer function associated with the bony member and the reference medium. The differential phase spectrum will be denoted by $\tau_g(f)$, and is given by $$\tau_g(f) = \frac{-L}{2\pi} \frac{d\beta(f)}{df} \quad (12)$$

where $\beta(f)=\arg[H(f)]/L$, $\arg[H(f)]$ evaluates the phase of the complex bone transfer function, $H(f)$, and $L$ is the thickness of the bony member. (It should be noted that $\beta(f)$ has no relation to the $\beta$ parameter defined in the above with the MIF. The differential phase can be further processed to obtain a set of polynomial coefficients, which can serve as inputs to the subsequent comparative analysis step, together with the signal parameters in $\Theta_s$ and $\Theta_r$. As yet an alternative embodiment, the differential phase can be further processed to obtain the group velocity, $v_g(f)$, associated with the bony member, which itself may be characterized by a set of polynomial coefficients. These coefficients, or the group velocity itself, can serve as inputs to the subsequent comparative analysis step, together with the signal parameters in $\Theta_s$ and $\Theta_r$.

It should also be pointed out that the parametric signal models disclosed here, and most particularly those represented by Equations (1–2), are phase sensitive in the sense that they depend not only on the amplitude spectrum of the ultrasound signals, but also on the phase spectrum. Specifically, the reduced set of parameters associated with the bone tissue and coming out as a result of the preprocessing step is phase sensitive (phase responsive). This phase sensitive nature extends beyond that represented by the pure time delays (as provided by estimates of $\tau_s$ and $\tau_r$), but includes also that represented by the phase spectrum of the signal model itself. Therefore, it should be noted that the current invention allows for amplitude and phase information to be compared and used for the diagnosis of bone condition. This information is contained in the bone-oriented and reference ultrasound signal parameter sets $\{A_{s0}, A_{s1}, \ldots A_{si}, a_s, f_s, \tau_s\}\{K_{s0}, K_{s1}, \ldots K_{sm}, b_s, f_s, \tau_s\}$ and $\{A_{s0}, A_{r1}, \ldots A_{rj}, a_r, f_r, \tau_r\}\{K_{r0}, K_{r1}, \ldots K_{rq}, b_r, f_r, \tau_r\}$, respectively.

In another embodiment of the invention, transducers 16 and 18 in FIG. 1 are multi-element, two-dimensional array transducers. In a presently preferred embodiment, each transducer 16, 18 is rectangular, 3 cm by 4 cm, comprised of 10×13 (−2)=128 elements (two corner elements not being used), with nominal center frequency of 850 kHz and bandwidth 80%. These transducers may suitably be obtained from Parallel Designs, Inc. of Phoenix, Ariz. As mentioned supra, the excitation signal generated by card 24 serves as input to power amplifier means 26. The output of power amplifier means 26 then passes through switching network 27a before reaching transducer 16. Signals received at transducer 18 must similarly pass through switching network 27b before card 28 receives them. Switching network 27a is a signal routing and measurement switch which sequentially connects the single channel output of the waveform generator card 24 via power amplifier means 26 to each of the elements of the launch transducer 16. Switching network 27b similarly connects the single channel input of card 28 to each of the elements of the receiving transducer 18. Networks 27a and 27b may suitably be test system switch products of Hewlett-Packard Co., Santa Clara, Calif., identified by Hewlett-Packard part No. HP 3235A. This switch unit provides capability for switching literally thousands (for this model a total of 20,480) of two-wire analog points, under computer control via a general purpose interface bus (GPIB) 29, shown as a dashed line in FIG. 1.

Figure 5:
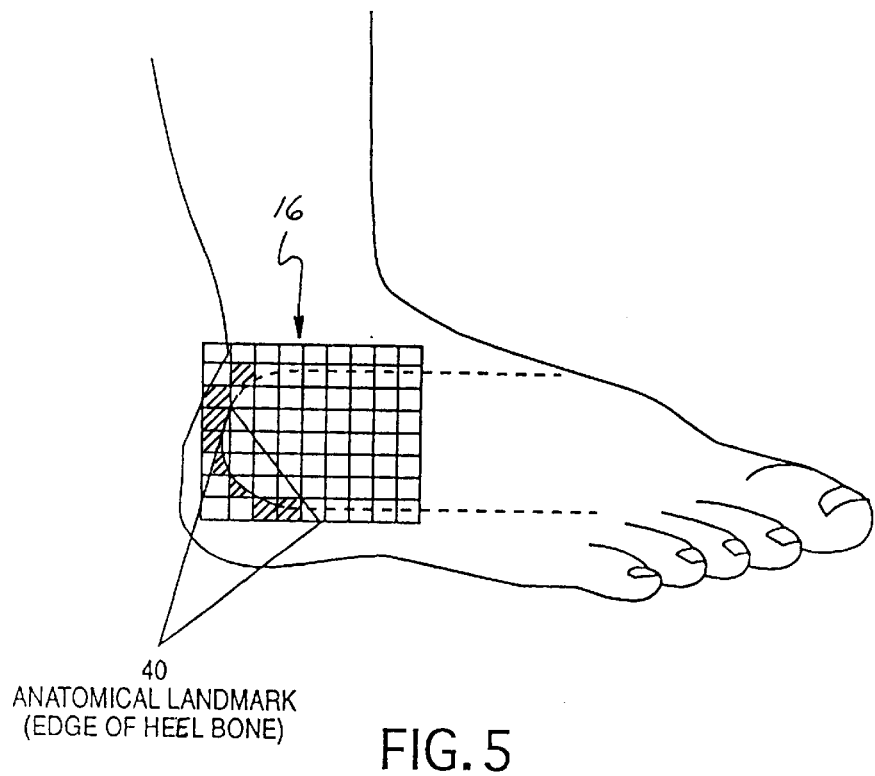
FIG. 5 is a drawing of a multi-element, two-dimensional array transducer on one side of the calcaneus, or heel, bone.

As shown in FIG. 5, this alternative embodiment allows a predetermined anatomical landmark to be reliably located automatically through the use of signal processing rather than by physically repositioning the transducers 16 and 18 (one transducer not shown) relative to the anatomical region. The anatomical landmark can, for example, be the edge of a heel bone 40. Locating such a landmark can be accomplished because the parameters disclosed in the present invention are strongly dependent on the type of tissue (soft tissue vs. bone) through which the ultrasound signal is propagated. For example, the mean instantaneous frequency is much higher when the ultrasound signal travels through the soft tissue laterally surrounding the bone as compared to the bone itself (typically 600 kHz for soft tissue vs. 300 kHz for bone). In addition, there are dramatic shifts in relative pulse width and in envelope velocity. By locating anatomical landmarks in this fashion, improved reproducibility and precision in ultrasound parameter estimates can be accomplished. In one preferred embodiment, data obtained through the ultrasonic interrogation of the tissue can itself be used as local reference sites for reproducibly positioning the tissue relative to the transducers 16 and 18. The above embodiments utilizing "electronic" positioning can be implemented using suitable template matching and correlative techniques, as well as edge detection algorithms, well known in the art and as described in the book "Digital Image Processing," by Gonzales and Wintz, 2d ed. (1981), Addison-Wesley, Redding, Mass. which is fully incorporated herein by reference. It should be understood that all of the techniques disclosed herein, including, but not limited to zero-crossing analysis and the envelope detection-analysis methods, and all of the parameters disclosed herein, including, but not limited to mean-instantaneous frequency, envelope time duration, overall energy content and time delays are directly applicable and useful and preferred for use with multi-element, two-dimensional array transducers.

The utilization of multi-element, two-dimensional array transducers 16 and 18, also allows the averaging of a large set of data from a plurality of excitation signals which can lead to more accurate estimates of bone density, strength, and fracture risk, and also improve the capacity for reliable intrapatient and interpatient comparisons. Furthermore, each element of each transducer 16, 18 can be operated in pulse-echo mode, enabling the soft tissue thicknesses overlying a bone to be measured. For this purpose an ultrasonic pulser-receiver card can be added to the computer 20. The pulser-receiver card can be suitably a Matec Instruments, Inc., of Northborough, Mass., Model No. SR-9000.

Finally, in an alternative embodiment, the multi-element, two-dimensional array transducers 16 and 18 can be utilized in a synthetic array aperture mode. In this mode a single excitation signal is passed through a plurality of the array elements, also known as the aperture. By moving the entire aperture one element at a time across the array, high resolution images are made possible, but a high signal to noise ratio can also still be maintained and beam divergence reduced. For this embodiment, the switching networks 27a and 27b may be replaced by a relay-based system, which allows more flexibility in terms of switching capabilities. The relay system may be suitably Model No. JX/256 manufactured by Cytec Corp. of Penfield, N.Y. Additional information which may be useful in this approach is "Synthetic Aperture Radar," by Curlander and McDonough, John Wiley, 1991, the entire disclosure of which is incorporated herein by reference.

Figure 6:
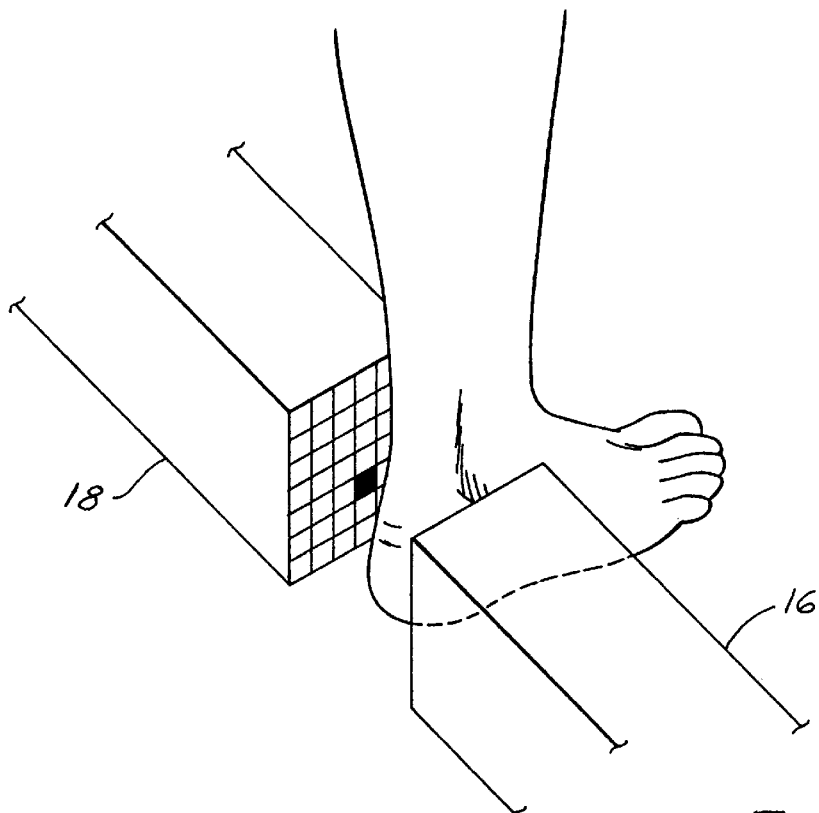
FIGS. 6–7 are perspective views showing a single-element transducer and an array transducer on opposite sides of the heel of a human foot.
Figure 7:
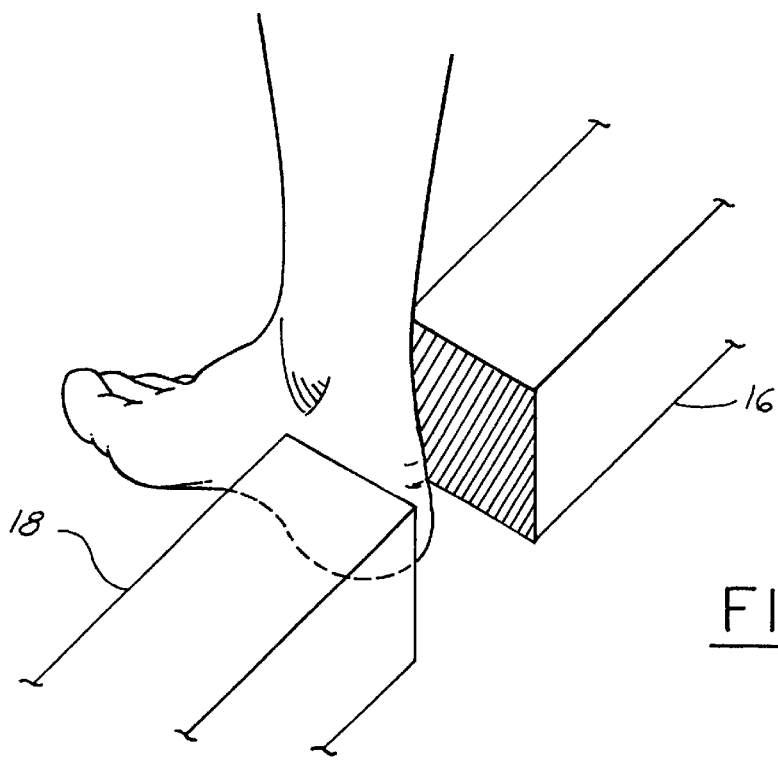

In yet another alternative embodiment, only one of transducers 16, 18 is an array transducer—preferably transducer 18—as illustrated in FIGS. 6–7. In this single-array transducer embodiment, transducer 16 may be a 1 MHZ nominal frequency 1.5 inch diameter transducer, Model No. 392, from Panametrics, Inc. of Waltham, Mass. while transducer 18 may be a 850 kHz nominal center frequency, 3 cm×4 cm rectangular array transducer having 128, 3 mm×3 mm elements from Acoustic Imaging of Phoenix, Ariz. In general, transducer 16 should be large enough to cover a region which is of clinical interest and which may also include some anatomical landmarks to be used in repositioning transducer 16. Transducer 18 should be approximately the same size as transducer 16, although the size and shape of the transducers relative to each other may vary. Nevertheless, transducers 16 and 18 should overlap in a region sufficiently large to obtain enhanced reproducibility and accuracy. With respect to the heel region illustrated in FIGS. 6–7, such a region may be several centimeters in size. However, other anatomical sites, such as a finger, may utilize a smaller region of overlap. Finally, because transducer 16 is a single-element transducer, switcher 27a is not required in the single-array transducer embodiment.

The single-array transducer embodiment is much easier to implement and is much less expensive than the dual-array embodiment described hereinabove, yet retains most of the advantages of the dual-array embodiment, in terms of enhanced reproducibility and accuracy, as compared to embodiments employing a pair of single-element transducers. It should be understood that the single-array transducer embodiment, like the dual-array transducer embodiment, can be used with a variety of signal processing techniques, including transit-time and attenuation slope techniques such as BUA, as well as the parametric modeling technique disclosed herein. It should also be understood that, depending on the signal processing technique utilized, the single-array transducer embodiment may or may not include means for, or the step of, directing the ultrasound signal through a known medium to obtain a reference electrical output signal.

While several embodiments of the present invention have been disclosed hereinabove, it is to be understood that these embodiments are given by example only and not in a limiting sense. Those skilled in the art may make various modifications and additions to the preferred embodiments chosen to illustrate the invention without departing from the spirit and scope of the present contribution to the art. Accordingly, it is to be realized that the patent protection sought and to be afforded hereby shall be deemed to extend to the subject matter claimed and all equivalence thereof fairly within the scope of the invention.

What we claim is:

1. A method of non-invasive and quantitative assessment of the status of bone tissue in vivo for at least one of the quantities, bone-mineral density, bone strength, bone fracture risk, bone architecture and bone quality comprising the steps of:

acoustically coupling a first transducer and a second transducer to nearby skin on opposite sides of said bone tissue wherein one of said first and second transducers is a single-element transducer and another of said first and second transducers is an array transducer;

generating an ultrasound signal and directing said ultrasound signal from said first transducer to said second transducer through said bone tissue to obtain a bone-oriented output signal; and processing said bone-oriented output signal whereby an estimate of said at least one of the quantities, bone-mineral density, bone strength, bone fracture risk, bone architecture and bone quality is obtained.

2. The method of claim 1 wherein said processing step includes determining a transit time of said ultrasound signal through said bone tissue.

3. The method of claim 1 wherein said processing step includes determining a velocity of said ultrasound signal through said bone tissue.

4. The method of claim 1 wherein said processing step includes determining an attenuation slope associated with said ultrasound signal.

5. The method of claim 1 further comprising the step of independently directing said ultrasound signal from said first transducer to said second transducer through a medium with known acoustic properties and path length and free of said bone tissue to produce a reference electrical output signal and wherein said processing step includes establishing a set $\Theta_s$ of bone-oriented parameters associated with said bone-oriented output signal and a set $\Theta_r$ of reference parameters associated with said reference signal and subjecting said set $\Theta_s$ of bone-oriented parameters and said set $\Theta_r$ of reference parameters to comparative analysis.

6. The method of claim 1 wherein said second transducer is said array transducer.

7. An apparatus for non-invasive and quantitative assessment of the status of bone tissue in vivo for at least one of the quantities, bone-mineral density, bone strength, bone fracture risk, bone architecture and bone quality comprising:

first and second transducers wherein one of said first and second transducers is a single-element transducer and another of said first and second transducers is an array transducer;

means for generating an ultrasound signal and directing said ultrasound signal from said first transducer to said second transducer through said bone tissue to obtain a bone-oriented output signal; and means for processing said bone-oriented output signal whereby an estimate of said at least one of the quantities, bone-mineral density, bone strength, bone fracture risk, bone architecture and bone quality is obtained.

8. The apparatus of claim 7 wherein said second transducer is said array transducer.

9. A method of non-invasive and quantitative assessment of the status of bone tissue in vivo for at least one of the quantities, bone-mineral density, bone strength, bone fracture risk, bone architecture and bone quality comprising the steps of:

acoustically coupling a pair of transducers to nearby skin on opposite sides of said bone tissue;

generating an ultrasound signal and directing said ultrasound signal from one transducer of said pair of transducers to another transducer of said pair of transducers through said bone tissue, to produce a bone-oriented electrical output signal;

independently directing said ultrasound signal from said one transducer to said another transducer through a medium with known acoustic properties and path length and free of said bone tissue to produce a reference electrical output signal;

establishing a set $\Theta_s$ of bone-oriented parameters associated with said bone-oriented output signal and a set $\Theta_r$ of reference parameters associated with said reference signal; and subjecting said set $\Theta_s$ of bone-oriented parameters and said set $\Theta_r$ of reference parameters to comparative analysis, whereby an estimate of said at least one of the quantities, bone-mineral density, bone strength, bone fracture risk, bone architecture and bone quality is obtained.

10. The method of claim 9 wherein said another transducer is an array transducer.

11. The method of claim 10 wherein said one transducer is an array transducer.

12. A method of non-invasive and quantitative assessment of the status of bone tissue in vivo for at least one of the quantities, bone-mineral density, bone strength, bone fracture risk, bone architecture and bone quality comprising the steps of:

(a) acoustically coupling a pair of transducers to nearby skin on opposite sides of said bone tissue;

(b) generating an ultrasound signal and directing said ultrasound signal from one transducer of said pair of transducers to another transducer of said pair of transducers through said bone tissue, to produce a bone-oriented electrical output signal;

(c) repeating said step (b) a plurality of times to obtain a plurality of bone-oriented output signals;

(d) averaging said plurality of bone-oriented output signals to obtain an averaged bone-oriented output signal;

(e) independently directing said ultrasound signal from said one transducer to said another transducer through a medium with known acoustic properties and path length and free of said bone tissue to produce a reference electrical output signal;

(f) repeating said step (e) a plurality of times to obtain a plurality of reference signals;

(g) averaging said plurality of reference signals to obtain an averaged reference signal;

(h) establishing a set $\Theta_s$ of bone-oriented parameters associated with said averaged bone-oriented output signal and a set $\Theta_r$ of reference parameters associated with said averaged reference signal; and (i) subjecting said set $\Theta_s$ of bone-oriented parameters and said set $\Theta_r$ of reference parameters to comparative analysis whereby an estimate of said at least one of the quantities, bone-mineral density, bone strength, bone fracture risk, bone architecture and bone quality is obtained.

13. The method of claim 12 wherein said another transducer is an array transducer.

14. The method of claim 13 wherein said one transducer is an array transducer.

15. A method of non-invasive and quantitative assessment of the status of bone tissue in vivo for at least one of the quantities, bone-mineral density, bone strength, bone fracture risk, bone architecture and bone quality comprising the steps of:

(a) acoustically coupling a first transducer and a second transducer to nearby skin on opposite sides of said bone tissue, wherein said second transducer is an array transducer;

(b) generating an ultrasound signal and directing said ultrasound signal from said first transducer to an element of said second transducer through said bone tissue to produce a bone-oriented electrical output signal;

(c) independently directing said ultrasound signal from said first transducer to said element of said second transducer through a medium with known acoustic properties and path length and free of said bone tissue to produce a reference electrical output signal;

(d) establishing a set $\Theta_s$ of bone-oriented parameters associated with said bone-oriented output signal and a set $\Theta_r$ of reference parameters associated with said reference signal;

(e) repeating said step (b), said step (c), and said step (d) at least one time wherein said ultrasound signal is directed in said step (b) and said step (c) from said first transducer to a previously unselected element of said second transducer to thereby create a plurality of sets $\Theta_s$ of bone-oriented parameters and a plurality of sets $\Theta_r$ of reference parameters;

(f) evaluating said plurality of sets $\Theta_s$ of bone-oriented parameters to locate an anatomical region; and (g) subjecting at least one set $\Theta_s$ of said plurality of sets $\Theta_s$ of bone-oriented parameters, said one set $\Theta_s$ corresponding to said anatomical region, and at least one set $\Theta_r$ of said plurality of sets $\Theta_r$ of reference parameters to comparative analysis, whereby an estimate of said at least one of the quantities, bone-mineral density, bone strength, bone fracture risk, bone architecture and bone quality is obtained.

16. An apparatus for non-invasive and quantitative assessment of the status of bone tissue in vivo for at least one of the quantities, bone-mineral density, bone strength, bone fracture risk, bone architecture, and bone quality comprising first and second transducers;

means for generating an ultrasound signal, directing said ultrasound signal from said first transducer to said second transducer through said bone tissue to produce a bone-oriented electrical output signal, and independently directing said ultrasound signal from said first transducer to said second transducer through a medium of known acoustic properties and path length and free of said bone tissue to produce a reference electrical output signal; and means for establishing a set $\Theta_s$ of bone-oriented parameters associated with said bone-oriented output signal and a set $\Theta_r$ of reference parameters associated with said reference signal and performing comparative analysis of said set of bone-oriented parameters $\Theta_s$ and said set of reference parameters $\Theta_r$ to thereby obtain an estimate of said at least one of the quantities, bone-mineral density, bone strength, bone fracture risk, bone architecture and bone quality.

17. The apparatus of claim 16 wherein said second transducer is an array transducer.

18. The apparatus of claim 17 wherein said first transducer is an array transducer.

* * * * *